United States Patent [19]
Yoshinari et al.

[11] Patent Number: 6,136,762
[45] Date of Patent: Oct. 24, 2000

[54] METHOD FOR PREPARING UREA GREASE HAVING LOW NOISE PROPERTIES

[75] Inventors: Terasu Yoshinari; Yuji Onuki; Yoichi Suzuki; Hiroshi Kimura, all of Fujisawa, Japan

[73] Assignee: Kyodo Yushi Co., Ltd., Tokyo, Japan

[21] Appl. No.: 09/514,293

[22] Filed: Feb. 28, 2000

[30] Foreign Application Priority Data

Mar. 3, 1999 [JP] Japan .................................. 11-055730

[51] Int. Cl.⁷ ................................................ C10M 115/08
[52] U.S. Cl. .............................................................. 508/552
[58] Field of Search ............................................. 508/552

[56] References Cited

U.S. PATENT DOCUMENTS

| | | |
|---|---|---|
| 2,925,387 | 2/1960 | Traise et al. . |
| 4,668,411 | 5/1987 | Yasui et al. .............................. 508/552 |
| 5,707,944 | 1/1998 | Yokouchi et al. ....................... 508/552 |
| 6,063,743 | 5/2000 | Seubert et al. .......................... 508/552 |

FOREIGN PATENT DOCUMENTS

| | | |
|---|---|---|
| 63-162790 | 7/1988 | Japan . |
| 01139696 | 6/1989 | Japan . |
| 2-4895 | 1/1990 | Japan . |
| 3-190996 | 8/1991 | Japan . |

*Primary Examiner*—Jacqueline V. Howard
*Attorney, Agent, or Firm*—Oblon, Spivak, McClelland, Maier & Neustadt, P.C.

[57] ABSTRACT

A method for preparing urea grease excellent in low noise properties comprises the step of adding a base oil in which an amine (or an isocyanate) is dissolved or dispersed, to a base oil in which an isocyanate (or an amine) is dissolved or dispersed, in the form of liquid drops having a diameter of not more than 300 $\mu$m to react the isocyanate with the amine; or the step of directly contacting liquid drops comprising a base oil in which an isocyanate is dissolved or dispersed and having a diameter of not more than 300 $\mu$m with liquid drops comprising a base oil in which an amine is dissolved or dispersed and having a diameter of not more than 300 $\mu$m to react the isocyanate with the amine. The method permits the production of urea grease excellent in low noise properties at a low cost.

9 Claims, No Drawings

METHOD FOR PREPARING UREA GREASE HAVING LOW NOISE PROPERTIES

BACKGROUND OF THE INVENTION

1. Field of the Invention

The present invention relates to a method for preparing grease having excellent low noise properties. More specifically, the present invention pertains to a method for preparing grease which is suitable for sealing in motorcar parts for electric motor-operated devices such as an alternator, a solenoid-operated clutch for car air conditioners, an idle pulley, an intermediate pulley, an electric fan motor, a fluid coupling, a water pump, a distributor and a starter one-way clutch; rolling bearings, for instance, rolling bearings used at a high temperature and a high rotational speed such as auxiliary machinery for engines, rolling bearings used in household electric articles at a high temperature and a high rotational speed such as cleaner motors and air conditioner fan motors, rolling bearings used in spindle motors for recording devices such as computer hard disks and CD-R's and those for other widely used motors.

2. Description of the Prior Art

Principal factors for the improvement of the low noise properties of grease are, for instance, to uniformly disperse a thickener in the grease and to eliminate impurities present therein. Thickeners for greases may be classified into those completely soluble in a base oil and those hardly soluble therein when the temperature is raised during the preparation of the grease. Urea thickeners which are reaction products of an isocyanate and an amine are also classified into those completely soluble in a base oil and those hardly soluble therein.

As an example, Japanese Un-Examined Patent Publication (hereinafter referred to as "J.P. KOKAI") No. Sho 63-162790 discloses a means for the improvement of the low noise properties of completely soluble urea thickener-containing grease. More specifically, this patent discloses a method which comprises the steps of dissolving urea grease comprising a specific combination of ingredients in a lubricating oil and then passing the resulting solution through a filter to thus remove the impurities included therein. Since the thickener is completely dissolved in a base oil, this method may ensure the uniform dispersion of the thickener and also permits the removal of the impurities present therein by passing it through a filter. On the other hand, improvement of the low noise properties of hardly soluble urea thickener-containing grease is disclosed in Japanese Patent Application Serial No. Sho 63-153654 (J.P. KOKAI Hei 2-4895), which discloses that a thickener component can uniformly be dispersed in a base oil and the low noise properties of the resulting grease can thus be improved by subjecting the grease to a milling treatment after the completion of the reaction process.

In addition, J.P. KOKAI No. Hei 3-190996 discloses a method in which the low noise properties of grease can considerably be improved by using a mixing head as a reaction vessel and by reacting the isocyanate with the amine under a high pressure condition to thus uniformly disperse the resulting urea thickener in the grease.

However, recent grease has been required to satisfy increasingly severe requirements for low noise properties and the conventional methods have not been able to prepare any grease having the required low noise properties. For instance, in the method disclosed in Japanese Patent Application Serial No. Sho 63-153654 (J.P. KOKAI No. Hei 2-4895), the size of the thickener particles in the urea grease is determined simultaneous with the micelle formation during the reaction and therefore, it is impossible to further divide the resulting huge micelles into fine particles to thus obtain a uniformly dispersion by a subsequent milling treatment. For this reason, the conventional methods have never been able to provide any grease satisfying these severe requirements for low noise propertes.

Moreover, the method disclosed in J.P. KOKAI No. Hei 3-190996 permits the production of grease, which satisfies the foregoing severe requirements for low noise properties. However, the method requires a tremendous labor and is also very expensive.

In addition, the method disclosed in J.P. KOKAI No. Sho 63-162790 cannot be applied to the insoluble urea thickener-containing grease.

SUMMARY OF THE INVENTION

Accordingly, it is an object of the present invention to provide a novel method which can prepare urea grease having excellent low noise properties at a low cost.

The inventors of this invention have thus conducted various studies to eliminate the foregoing drawbacks associated with the conventional methods for preparing urea grease, have found that the drawbacks can be eliminated by previously adjusting the particle size of liquid drops used for forming an urea thickener and by appropriately devising the process for forming the urea thickener, to a predetermined level and have thus completed the present invention.

According to a first aspect of the present invention, there is provided a method for preparing grease excellent in low noise properties which comprises the step of adding a base oil in which an amine is dissolved or dispersed, to a base oil in which an isocyanate is dissolved or dispersed, in the form of liquid drops having a diameter of not more than 300 $\mu$m to react the isocyanate with the amine.

According to a second aspect of the present invention, there is provided a method for preparing grease excellent in low noise properties which comprises the step of adding a base oil wherein an isocyanate is dissolved or dispersed, to a base oil wherein an amine is dissolved or dispersed, in the form of liquid drops having a diameter of not more than 300 $\mu$m to react the amine with the isocyanate.

According to a third aspect of the present invention, there is provided a method for preparing grease excellent in low noise properties which comprises the step of directly contacting liquid drops comprising a base oil in which an isocyanate is dissolved or dispersed and having a diameter of not more than 300 $\mu$m with liquid drops comprising a base oil in which an amine is dissolved or dispersed and having a diameter of not more than 300 $\mu$m to react the isocyanate with the amine.

In these aspects, the diameter of the liquid drops is preferably not more than 100 $\mu$m.

DESCRIPTION OF THE PREFERRED EMBODIMENTS

The present invention will be described in more detail below.

The method of the present invention comprises, in the process for preparing urea grease, the step of adding a base oil (hereinafter referred to as "amine liquid") in which an amine is dissolved or dispersed, to a base oil (hereinafter referred to as "isocyanate liquid") in which an isocyanate is dissolved or dispersed, in the form of liquid drops having a diameter of not more than 300 μm and preferably not more than 100 μm to react the isocyanate with the amine; or the step of adding an isocyanate liquid to an amine liquid in the form of liquid drops having a diameter of not more than 300 μm and preferably not more than 100 μm to react the amine with the isocyanate; or the step of directly contacting liquid drops comprising an isocyanate liquid and having a diameter of not more than 300 μm, preferably not more than 100 μm with liquid drops comprising an amine liquid and having a diameter of not more than 300 μm, preferably not more than 100 μm to react the isocyanate with the amine, to thus reduce the particle size of the resulting urea thickener and to simultaneously permit the preparation of a uniform dispersion. Thus, the method of the present invention allows the formation of grease showing good low noise properties.

As base oils used in the urea grease of the present invention, there may be listed, for instance, mineral oils such as paraffinic mineral oils; ester type synthetic oils such as polyol ester oils; ether type synthetic oils such as alkyl diphenyl ethers; synthetic hydrocarbon oils such as poly(α-olefins); and carbonic acid ester compounds.

Examples of isocyanate compounds used in the method of the invention are diisocyanates such as phenylene diisocyanate, diphenyl diisocyanate, phenyl diisocyanate, diphenylmethane diisocyanate, tolylene diisocyanate, octadecane diisocyanate, decane diisocyanate and hexane diisocyanate.

In addition, examples of amines usable in the present invention are monoamines such as ammonia, octylamine, dodecylamine, hexadecylamine, octadecylamine, oleylamine, aniline, p-toluidine and cyclohexylamine; and diamines such as phenylenediamine, diphenylenediamine, ethylenediamine, propylenediamine, octylenediamine and octadecylenediamine.

In the method for preparing urea grease according to the present invention, the amount of monoamine to be used per mole of diisocyanate preferably ranges from about 1.9 to 2.1 moles and most preferably 2 moles, i.e., the stoichiometric amount.

In addition, the amounts of ammonia and monoamine to be used per 2 moles of diisocyanate preferably range from about 0.9 to 1.1 mole and about 1.9 to 2.1 moles and most preferably one mole and 2 moles, i.e., the stoichiometric amounts, respectively. Moreover, the amounts of monoamine and diamine to be used per 2 moles of diisocyanate range from about 1.9 to 2.1 moles and about 0.9 to 1.1 mole and most preferably 2 moles and one mole, i.e., the stoichiometric amounts, respectively.

The amount of isocyanate in the isocyanate liquid preferably ranges from 5 to 40% by weight and more preferably 5 to 30% by weight based on the total weight of the isocyanate liquid. Moreover, the amount of amine present in the amine liquid preferably ranges from 5 to 40% by weight and more preferably 5 to 30% by weight based on the total weight of the amine liquid.

When practicing the method according to the first aspect, various methods can be used as means for adding, to the isocyanate liquid, the amine liquid after forming the latter into liquid drops having a diameter of not more than 300 μm, preferably not more than 100 μm. Examples of such methods include a method in which an amine liquid is dropwise added to an isocyanate liquid while maintaining a desired diameter of the liquid drops by passing the amine liquid through holes having a predetermined diameter; a method comprising stirring an amine liquid using, for instance, a homogenizer to give liquid drops having a predetermined particle size and then adding the drops to an isocyanate liquid; a method comprising forming an amine liquid into liquid drops having a desired particle size by passing the liquid through, for instance, an appropriate mesh and then adding the drops to an isocyanate liquid; a method comprising injecting an amine liquid through injection nozzles at a predetermined pressure to form liquid drops of the amine liquid having a desired particle size and then adding the drops to an isocyanate liquid; a method comprising applying high frequency or ultrasonics to an amine liquid to convert it into mist or liquid drops having a desired particle size and then dispersing them in an isocyanate liquid.

The foregoing method according to the second aspect can be carried out by the same procedures used above in the practice of the method according to the first aspect except that the amine liquid and the isocyanate liquid are replaced with one another in the description of the first method.

Moreover, when the foregoing method according to the third aspect of the invention is carried out, it is sufficient to directly contact the amine liquid or the liquid drops thereof having a desired particle size and obtained according to the procedures used for carrying out the first method with liquid drops of the isocyanate liquid having a predetermined particle size and preferably directly collide the former with the latter.

Moreover, when the liquid drops of an amine liquid or an isocyanate liquid are formed using injection nozzles, the diameter of the nozzles is desirably not more than 5.0 mm and preferably not more than 3.0 mm. It is not needed to specifically define the lower limit of the nozzle diameter, but the nozzle diameter is in general not less than 0.1 mm. In addition, the cross sectional shape of the nozzles is not also limited to any specific one inasmuch as they can form liquid drops having a desired particle size. Further the pressure applied to the liquid upon spraying is desirably not less than 2.5 kgf/cm$^2$ and preferably not less than 5.0 kgf/cm$^2$. The upper limit of the pressure is not restricted to any specific level, but it is generally sufficient to use a pressure of not more than 50 kgf/cm$^2$.

The particle size of these liquid drops can be determined by using, for instance, a phase Doppler type radar particle size analyzer which has been used for the determination of the particle size of sprayed particles of, for instance, combustion oils for jet engines. The principle of this phase Doppler is to expose moving particles with laser rays, to receive a part of scattered light rays whose frequency is shifted and to process the resulting information by a computer to thus estimate the particle size.

However, the present invention is not restricted to these means for adding these liquid drops, for contacting them, for producing the same and for determining the particle size (and/or distribution thereof).

When adding an amine liquid (or an isocyanate liquid) to an isocyanate liquid (or an amine liquid), the latter is preferably stirred. The temperature of the amine liquid is preferably set at a level of from about 70 to 80° C., while that of the isocyanate liquid is adjusted to about 70 to 80° C. In addition, the reaction temperature of the amine with the isocyanate desirably ranges from 90 to 120° C. and the reaction time is desirably not more than 30 minutes. After the completion of the addition of the amine liquid (or the isocyanate liquid) or after the completion of the contact of the amine liquid with the isocyanate liquid, the mixture is further stirred for about 30 minutes to complete the reaction.

The amount of the urea thickener present in the urea grease of the present invention preferably ranges from 5 to 40% by weight and more preferably 5 to 30% by weight based on the total amount of the urea grease.

Moreover, the urea grease of the present invention may further comprise various additives widely used in this field, for instance, antioxidants such as amine type, phenolic, sulfur atom-containing antioxidants and zinc dithiophosphate; extreme pressure agents such as chlorine atom-containing, sulfur atom-containing type ones, zinc dithiophosphate and organomolybdenum compounds; rust proof agents such as petroleum sulfonate, dinonylnaphthalene sulfonate and sorbitan esters; metal deactivators such as benzotriazole and sodium nitlite; and viscosity index improvers such as poly(methacrylate), polyisobutylene and polystyrene.

The urea grease of the invention thus produced may further be processed using, for instance, Flymer mill Monton Goly mill or a three-stage roll mill.

As has been discussed above in detail and as will be proved by the following Examples and Comparative Examples, the method of the present invention permits the production of urea grease excellent in low noise properties at a low cost.

The present invention will hereinafter be described in more detail with reference to the following non-limitative working Examples and Comparative Examples. The details of Examples and Comparative Examples are summarized in the following Tables 1 and 2. The procedures of each test are as follows:

(i) Consistency of Mixture: This was determined according to JIS K 2220 5.3.

(ii) Particle Size of Urea Compound: This was determined by optical microscopic observation (X100 magnification).

(iii) Bearing Sound Test: This test was performed using Anderonmeter.

Test Conditions:

Bearing 608 was used; thrust load: 3 kgf; radial load: 0.15 kgf; number of revolutions: 1800 rpm; amount of filled grease: 0.35 ml; testing time: 2 minutes.

Evaluation:

The results were evaluated by points based on the number of noises and Anderon levels (graded based on 100 points). The sample having a rating of not less than 70 was judged as practically acceptable.

The following base oil was used in the following Examples and Comparative Examples:

Mineral oil: paraffinic mineral oil (10.5 $mm^2/s(100°\ C.)$)

ADE: alkyl diphenyl ether (13.0 $mm^2/s(100°\ C.)$)

EXAMPLE 1

To a first container, there were added 13.38 g of MDI (4,4'-diphenylmethane diisocyanate) and 138 g of the mineral oil and separately there were added, to a second container, 10.62 g of CHA (cyclohexylamine) and 138 g of the mineral oil, followed by heating these liquids to 70 to 80° C., control of the liquid drop particle size of the amine liquid included in the second container by the following two methods and addition thereof to the isocyanate liquid in the first container to cause a reaction of the amine with the isocyanate. The first liquid was stirred at a rate of 180 rpm using a stirring rod. The addition was completed within a predetermined time period, the reaction product was heated up to 140° C. and then allowed to stand at 140° C. for 30 minutes to give urea grease.

Method A:

The amine liquid (or the isocyanate liquid) was injected through injection nozzles having a nozzle diameter of 0.5 mm at a pressure of 10 $kgf/cm^2$ to form liquid drops having a particle size of not more than 100 µm and then the resulting liquid drops were dropwise added to the isocyanate liquid (or the amine liquid).

Method B:

The amine liquid (or the isocyanate liquid) was injected through injection nozzles having a nozzle diameter of 2.0 mm at a pressure of 10 $kgf/cm^2$ to form liquid drops having a particle size of not more than 250 µm and then the resulting liquid drops were dropwise added to the isocyanate liquid (or the amine liquid).

In these methods A and B, the particle size was determined using a Doppler type radar particle size analyzer.

EXAMPLE 2

To a first container, there were added 7.53 g of MDI and 138 g of the mineral oil, while separately there were added to a second container, 16.47 g of octadecylamine (ODA) and 138 g of the mineral oil and then the same procedures used in Example 1 were repeated to form urea grease.

EXAMPLE 3

To a first container, there were added 29.1 g of MDI and 123 g of the mineral oil, while separately there were added to a second container, 24.9 g of p-toluidine and 123 g of the mineral oil and then the same procedures used in Example 1 were repeated to form urea grease.

EXAMPLE 4

To a first container, there were added 14.73 g of MDI and 135 g of the mineral oil, while separately there were added to a second container, 15.27 g of octylamine and 135 g of the mineral oil and then the same procedures used in Example 1 were repeated to form urea grease.

EXAMPLE 5

To a first container, there were added 9.63 g of MDI and 138 g of the mineral oil, while separately there were added to a second container, 3.84 g of CHA, 10.53 g of ODA and 138 g of the mineral oil and then the same procedures used in Example 1 were repeated to form urea grease.

EXAMPLE 6

To a first container, there were added 9.63 g of MDI and 138 g of ADE, while separately there were added to a second container, 3.84 g of CHA, 10.53 g of ODA and 138 g of ADE and then the same procedures used in Example 1 were repeated to form urea grease.

EXAMPLE 7

To a first container, there were added 26.91 g of TDI (tolylene diisocyanate) and 120 g of the mineral oil, while separately there were added to a second container, 33.09 g of p-toluidine and 120 g of the mineral oil and then the same procedures used in Example 1 were repeated to form urea grease.

EXAMPLE 8

To a first container, there were added. 13.38 g of MDI and 138 g of the mineral oil and separately there were added to a second container, 10.62 g of CHA and 138 g of the mineral oil, followed by heating these liquids to 70 to 80° C., control of the liquid drop particle size of the isocyanate liquid included in the first container by the foregoing method A or B and addition thereof to the amine liquid in the second container to cause a reaction of the amine with the isocyanate. The liquid in the second container was stirred at a rate of 180 rpm using a stirring rod. Then the same procedures used in Example 1 were repeated to form urea grease.

EXAMPLE 9

To a first container, there were added 13.38 g of MDI and 138 g of the mineral oil and separately there were added to a second container, 10.62 g of CHA and 138 g of the mineral oil, followed by heating these liquids to 70 to 80° C., control of the liquid drop particle size of these two liquids by the foregoing method A or B and collision of these liquid drops with each other in a third container to cause a reaction of the amine with the isocyanate. The liquid in the third container was stirred at a rate of 180 rpm using a stirling rod. Then the same procedures used in Example 1 were repeated to form urea grease.

COMPARATIVE EXAMPLE 1

To a first container, there were added 9.63 g of MDI and 138 g of the mineral oil and separately there were added to a second container, 3.84 g of CHA, 10.53 g of ODA and 138 g of the mineral oil, followed by heating these liquids to 70 to 80° C. and the addition of the amine liquid in the second container to the isocyanate liquid in the first container without any pre-treatment (method C) to cause a reaction of the amine with the isocyanate. Then the same procedures used in Example 1 were repeated to form urea grease.

COMPARATIVE EXAMPLE 2

To a first container, there were added 9.63 g of MDI and 138 g of ADE and separately there were added to a second container, 3.84 g of CHA, 10.53 g of ODA and 138 g of ADE. Thereafter the same procedures used in Comparative Example 1 were repeated to form urea grease.

COMPARATIVE EXAMPLE 3

To a first container, there were added 29.1 g of MDI and 123 g of the mineral oil and separately there were added to a second container, 24.9 g of p-toluidine and 123 g of the mineral oil. Thereafter the same procedures used in Comparative Example 1 were repeated to form urea grease.

COMPARATIVE EXAMPLE 4

To a first container, there were added 26.91 g of TDI and 120 g of the mineral oil and separately there were added to a second container, 33.09 g of p-toluidine and 120 g of the mineral oil. Thereafter the same procedures used in Comparative Example 1 were repeated to form urea grease.

COMPARATIVE EXAMPLE 5

To a first container, there were added 14.73 g of MDI and 135 g of the mineral oil and separately there were added to a second container, 15.27 g of octylamine and 135 g of the mineral oil. Thereafter the same procedures used in Comparative Example 1 were repeated to form urea grease.

COMPARATIVE EXAMPLE 6

To a first container, there were added 19.63 g of MDI and 138 g of the mineral oil and separately there were added to a second container, 3.84 g of CHA, 10.53 g of ODA and 138 g of the mineral oil, followed by heating these liquids to 70 to 80° C. The amine liquid contained in the second container was injected through injection nozzles having a nozzle diameter of 2.0 mm at a pressure of 2 kgf/cm$^2$ to form liquid drops having a particle size ranging from 500 to 450 μm and then the resulting liquid drops were dropwise added to the isocyanate liquid contained in the first container (method D) to cause a reaction of the amine with the isocyanate. Then the same procedures used in Example 1 were repeated to form urea grease.

The urea grease products prepared in the foregoing Examples and Comparative Examples were inspected for various properties using the procedures specified above. The results thus obtained are summarized in the following Tables 1 and 2. The data listed in these Tables clearly indicate that the method of the present invention could provide urea grease excellent in low noise properties.

TABLE 1-1

| Example No. | 1 | 2 | 3 | 4 | 5 |
|---|---|---|---|---|---|
| Composition of Thickener | | | | | |
| Diisocyanate: (wt %) | | | | | |
| MDI | 4.46 | 2.51 | 9.70 | 4.91 | 3.21 |
| TDI | — | — | — | — | — |
| Monoamine: (wt %) | | | | | |
| CHA | 3.54 | — | — | — | 1.28 |
| ODA | — | 5.49 | — | — | 3.51 |
| p-TO | — | — | 8.30 | — | — |
| OCA | — | — | — | 5.09 | — |
| Kind of Base Oil: (wt %) | | | | | |
| M.O. | 92 | 92 | 82 | 90 | 92 |
| ADE | — | — | — | — | — |
| Method for Pulverization | A/B | A/B | A/B | A/B | A/B |
| Liquid Drop Size (μm) of Amine Liquid (or Isocyanate Liquid) | 100>/250> | 100>/250> | 100>/250> | 100>/250> | 100>/250> |
| Worked Penetration | 301/304 | 305/298 | 258/264 | 272/278 | 268/258 |
| Particle Size of Urea Compound (μm) | 50>/100> | 50>/100> | 50>/100> | 50>/100> | 50>/100> |
| Bearing Sound Test | 81/80 | 86/81 | 80/79 | 84/80 | 86/81 |

TABLE 1-2

| Example No. | 6 | 7 | 8 | 9 |
|---|---|---|---|---|
| Composition of Thickener | | | | |
| Diisocyanate (wt %) | | | | |
| MDI | 3.21 | — | 4.46 | 4.46 |
| TDI | — | 8.97 | — | — |
| Monoamine (wt %) | | | | |
| CHA | 1.28 | — | 3.54 | 3.54 |
| ODA | 3.51 | — | — | — |
| p-TO | — | 11.03 | — | — |
| OCA | — | — | — | — |
| Kind of Base Oil: | | | | |
| M.O. | — | 80 | 92 | 92 |
| ADE | 92 | — | — | — |
| Method for Pulverization | A/B | A/B | A/B | A/B |
| Liquid Drop Size (μm) of Amine Liquid (or Isocyanate Liquid) | 100>/250> | 100>/250> | 100>/250> | 100>/250> |
| Worked Penetration | 266/260 | 267/259 | 310/311 | 305/310 |
| Particle Size (μm) of Urea Compound | 50>/100> | 50>/100> | 50>/100> | 50>/100> |
| Bearing Sound Test | 86/83 | 81/75 | 85/86 | 86/87 |

TABLE 2

| Comp. Ex. No. | 1 | 2 | 3 | 4 | 5 | 6 |
|---|---|---|---|---|---|---|
| Composition of Thickener | | | | | | |
| Diisocyanate (wt %) | | | | | | |
| MDI | 3.21 | 3.21 | 9.70 | — | 4.91 | 3.21 |
| TDI | — | — | — | 8.97 | — | — |
| Monoamine (wt %) | | | | | | |
| CHA | 1.28 | 1.28 | — | — | — | 1.28 |
| ODA | 3.51 | 3.51 | — | — | — | 3.51 |
| p-TO | — | — | 8.30 | 11.03 | — | — |
| OCA | — | — | — | — | 5.09 | — |
| Kind of Base Oil (wt %) | | | | | | |
| M.O. | 92 | — | 82 | 80 | 90 | 92 |
| ADE | — | 92 | — | — | — | — |
| Method for Pulverization | C | C | C | C | C | D |
| Amine Liquid Drop Particle Size ($\mu$m) | 1000< | 1000< | 1000< | 1000< | 1000< | 500> |
| Worked Penetration | 266 | 261 | 251 | 260 | 272 | 267 |
| Particle Size of Urea Compound ($\mu$m) | 200< | 200< | 200< | 200< | 200< | 200< |
| Bearing Sound Test | 0 | 0 | 0 | 0 | 0 | 30 |

MDI: 4,4'-diphenylmethane diisocyanate; TDI: tolylene diisocyanate; CHA: cyclohexylamine; ODA: octadecylamine; p-TO: p-toluidine; OCA: octylamine; M.O.: mineral oil; ADE: alkyl diphenyl ether.

What is claimed is:

1. A method for preparing grease excellent in low noise properties comprising the step of adding a base oil in which an amine is dissolved or dispersed, to a base oil in which an isocyanate is dissolved or dispersed, in the form of liquid drops having a diameter of not more than 300 $\mu$m to react the isocyanate with the amine.

2. The method of claim 1 wherein the diameter of the liquid drops is not more than 100 $\mu$m.

3. The method of claim 1 wherein the amount of the isocyanate present in the isocyanate liquid ranges from 5 to 40% by weight based on the total weight of the isocyanate liquid and the amount of the amine present in the amine liquid ranges from 5 to 40% by weight based on the total weight of the amine liquid.

4. A method for preparing grease excellent in low noise properties comprising the step of adding a base oil in which an isocyanate is dissolved or dispersed, to a base oil in which an amine is dissolved or dispersed, in the form of liquid drops having a diameter of not more than 300 $\mu$m to react the amine with the isocyanate.

5. The method of claim 4 wherein the diameter of the liquid drops is not more than 100 $\mu$m.

6. The method of claim 4 wherein the amount of the isocyanate present in the isocyanate liquid ranges from 5 to 40% by weight based on the total weight of the isocyanate liquid and the amount of the amine present in the amine liquid ranges from 5 to 40% by weight based on the total weight of the amine liquid.

7. A method for preparing grease excellent in low noise properties comprising the step of directly contacting liquid drops comprising a base oil in which an isocyanate is dissolved or dispersed and having a diameter of not more than 300 $\mu$m with liquid drops comprising a base oil in which an amine is dissolved or dispersed and having a diameter of not more than 300 $\mu$m to react the isocyanate with the amine.

8. The method of claim 7 wherein the diameter of the liquid drops is not more than 100 $\mu$m.

9. The method of claim 7 wherein the amount of the isocyanate present in the isocyanate liquid ranges from 5 to 40% by weight based on the total weight of the isocyanate liquid and the amount of the amine present in the amine liquid ranges from 5 to 40% by weight based on the total weight of the amine liquid.

* * * * *